United States Patent
Woo et al.

[11] 4,034,602
[45] July 12, 1977

[54] DYNAMIC MECHANICAL ANALYZER

[75] Inventors: Lecon Woo, Newark, Del.; John D. McGhee, Plymouth Meeting, Pa.

[73] Assignee: E. I. Du Pont de Nemours and Company, Wilmington, Del.

[21] Appl. No.: 662,269

[22] Filed: Feb. 27, 1976

[51] Int. Cl.² .................................... G01N 3/32
[52] U.S. Cl. .............................. 73/67.2; 73/15.6
[58] Field of Search ............ 73/100, 91, 15.6, 67.2, 73/101

[56] References Cited

U.S. PATENT DOCUMENTS

| | | | |
|---|---|---|---|
| 3,295,364 | 1/1967 | Van Dyke | 73/91 X |
| 3,324,714 | 6/1967 | Simon et al. | 73/100 |
| 3,751,977 | 8/1973 | Schilling, Jr. | 73/15.6 X |

FOREIGN PATENT DOCUMENTS

| | | | |
|---|---|---|---|
| 540,805 | 4/1929 | Germany | 73/100 |

Primary Examiner—Jerry W. Myracle

[57] ABSTRACT

An instrument for determining the complex mechanical response of samples incorporates two parallel sample arms each pivotally mounted at their central portion by flexure pivots of precisely known spring constants. The sample is mounted on one end of each. An electromechanical driver acts on the other end of one arm to maintain the arms and sample in mechanical oscillation about the pivots. A displacement transducer senses the mechanical motion. A feedback amplifier between the displacement transducer and the driver maintains the oscillation at a constant amplitude and at a resonant frequency determined primarily by the sample. With this arrangement the driver and displacement sensor are removed from the sample and its usual thermal chamber. This improves the stability of the instrument. At the same time the arms are dynamically balanced about the pivots and hence are relatively insensitive to vibrational upset.

15 Claims, 4 Drawing Figures

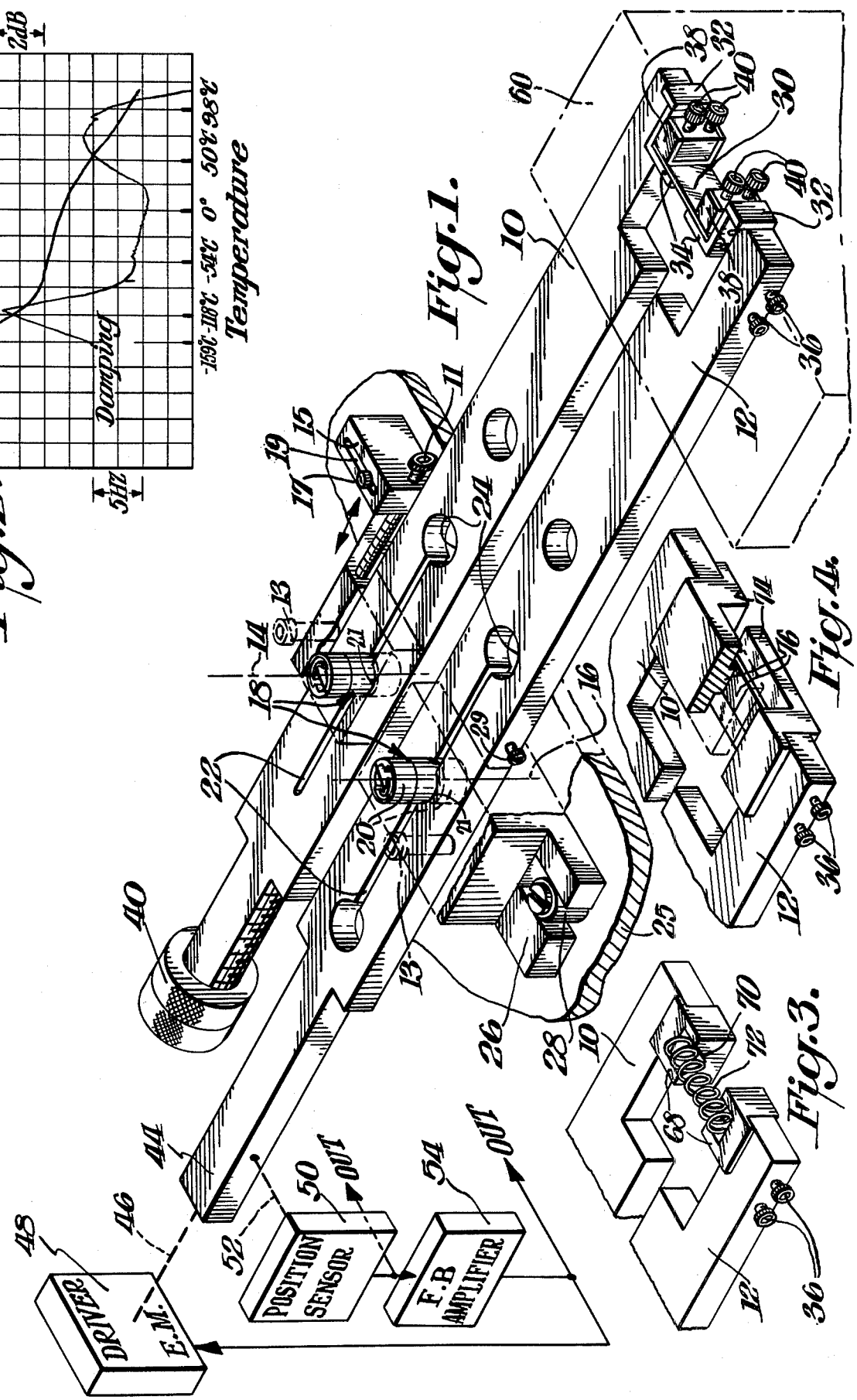

DYNAMIC MECHANICAL ANALYZER

BACKGROUND OF THE INVENTION

For many materials, including practically every man-made synthetic material, the mechanical behavior during processing as well as end product conditions is an important parameter that must be tightly specified and controlled. During the initial phases in the development of a new polymer or process, an understanding of the relationship between chemical structure and the physical properties of the process is of vital concern. Later on, in the process and quality control stages, factors such as mechanical strength, dimensional and thermal stability, and impact resistance are of utmost importance.

Virtually all synthetic materials in existence are viscoelastic, i.e., their behavior under mechanical stress lies somewhere between that of a pure viscous liquid and that of a perfectly elastic spring. Few materials behave like a perfect spring or a pure liquid. Rather, the mechanical behavior of these materials is generally time and/or temperature dependent and has led to such tests as creep, stress relaxation, tear, impact resistance, etc. One of the more important properties of materials sought is the materials' behavior under dynamic conditions. To explore this, a material's response to a cyclical stress as a function of temperature, time or frequency is determined. If a simple of a viscoelastic solid, for example is deformed and then released, a portion of the stored deformation energy will be returned at a rate which is a fundamental property of the material. That is, the sample goes into damped oscillation. A portion of the deformation energy is dissipated in other forms. The greater the dissipation, the faster the oscillation dies away. If the dissipated energy is restored the sample will vibrate at its natural (resonant) frequency. The resonant frequency is related to the modulus (stiffness) of the sample. Energy dissipation relates to such properties as impact resistance, brittleness, noise abatement, etc.

Because of their viscoelastic nature, the stress and strain in viscoelastic materials are not in phase, and, in fact, exhibit hysteresis. If a plot is made of this relationship, the area enclosed by the plot corresponds to the energy dissipated during each cycle of deformation of the material. In order to accurately describe this phenomenon, a complex modulus $E = E' + jE''$ is often used to characterize the material where E is Young's modulus, $E'$ is the real part and $E''$ is the imaginary part. The real part $E'$ of the modulus corresponds to the amount of energy that is stored in the strain and can be related to the spring constant, the complex part $E''$ corresponds to the energy dissipation or damping and can be related to the damping coefficient used in second order differential equations to define vibrating systems.

Many dynamic mechanical analyzers have been developed over the years for measuring these properties. A dynamic mechanical analyzer is an instrument for measuring the modulus and mechanical damping of a material as a function of temperature (or time). Unfortunately, most of these known analyzers have a relatively limited dynamic range. This severely limits the type of samples (modulus) that can be studied.

One such instrument is known as the torsion pendulum in which an inertia member is attached to a sample of carefully shaped geometry. The mechanical system is set into torsional oscillations by the operator or by a driving pulse and the amplitude of the resulting free decaying oscillation is recorded. The frequency of oscillation can be related to the complex shear modulus by known formulas and damping can be related to the logarithmic decrement in amplitude by other known formulas. While simple in concept, the torsional pendulum usually requires complex manipulations, high operator skill, and at least one man-day to obtain any meaningful data therefrom.

Another known dynamic mechanical analyzer, the Rheovibron, exercises the sample into periodic longitudinal extensions by an electromechanical drive. The input displacement and output force (strain and stress) are measured by two strain gauges. When the amplitude of the two vector quantities are equal, their algebraic difference is approximately equal to the tangent of delta (the angle of the vector E) when the angle is small. Unfortunately, this instrument, whereas simple again in the theory, has a number of disadvantages. One is that for high damping values, errors as great as 50% can and do occur. Further very precise near optical alignment of the shafts coupling to the sample is required. Finally, the sample must be strained to near its yield point on the stress/strain curve. For many viscoelastic samples, this is a nearly impossible condition to fulfill.

A major improvement over these prior art instruments was made by Shilling with a dynamic mechanical analyzer. Shilling clamps a sample between the ends of two rigidly mounted tines. The bent thus formed is set into vibration at its resonant frequency, which is determined partially by the sample, and subjects the sample under test to a shear stress. This system is somewhat limited in the minimum frequencies over which it can operate by the stiffness of the tines. Furthermore, since the drive must be separated from the sample region which typically is held in an oven or other thermal enclosure, an excessive amount of power is required to drive the system. Finally, the unit is not dynamically balanced and hence is easily upset by vibration and spurious vibration modes.

Accordingly, it is an object of this invention to obviate many of the disadvantages of the prior art dynamic mechanical analyzers.

Another object of this inventin is to provide an improved dynamic mechanical analyzer which is capable of operating over a wide dynamic range.

An additional object of this invention is to provide an improved dynamic mechanical analyzer in which the sample under test contributes more to the analyzer's operation.

BRIEF DESCRIPTION OF THE INVENTION

In accordance with a preferred embodiment of the invention, an apparatus for analyzing the dynamic properties of a sample is constructed having a pair of spaced, elongated members for engaging the sample therebetween, pivot means pivotally mounting the elongated members for lateral pivotal motion in a common plane, drive means for subjecting one of the members and hence through the sample, the other of said members to vibratory motion in plane, and sensing means responsive to the movement of one of the members for determining the dynamic properties of the sample.

By centrally locating flexure pivots having a known spring constant on each member and dynamically balancing the members, the sample may be located at one end of the members and the drive means and sensor means positioned at the other end such that they are less affected by the heat and cold of the sample chamber. The mechanical system is less easily upset by vibrations than would otherwise be the case. Furthermore, the analyzer is capable of operating over a relatively wide dynamic range and down to an oscillation frequency of as low as 1 or 2 Hertz. Sample influence upon the vibrational frequency is much greater. Since the motion of the entire system is geometrically centered at precisely known pivot points, both damping (E″) and linear modulus (E′) can be determined over a range of several decades. The simplified system with the fixed pivot point facilitates calculations.

DESCRIPTION OF THE DRAWINGS

The present invention can best be described with reference to the following FIGURES in which:

FIG. 1 is a partial pictorial, partial block representation of a dynamic mechanical analyzer constructed in accordance with a preferred embodiment of this invention;

FIG. 2 is a plot of frequency and damping as the ordinate against temperature as the abscissa depicting a typical response of a sample under varying temperature conditions;

FIG. 3 is a fragmentary view of an alternative sample holder that may be utilized with the analyzer of FIG. 1 for fluid materials which undergo transitions to solid state; and FIG. 4 is a fragmentary view of a sample holder that may be used with the analyzer of FIG. 1 with low viscosity samples.

DETAILED DESCRIPTION OF THE PREFERRED EMBODIMENTS

There may be seen in FIG. 1 a pictorial representation of a dynamic mechanical analyzer in which first and second elongated sample members or arms 10 and 12, respectively, are pivotally mounted at corresponding center pivot points 14 and 16, respectively, such that each may undergo pivotal movement in a common plane - in this case a generally horizontal plane. Preferably the plane should be situated such that gravity does not affect the movement of the arms. The arms constitute a driven arm 10 and a driving arm 12 as will be described. It is to be understood that the arm 10 and 12 may be pivoted in planes other than horizontal and in fact need not lie precisely in the same plane although this is much preferred since as the arms move in other than the same plane, the stesses applied to the sample, as will be described below, become more complex and introduce errors into the results. Pivoting preferably is accomplished by the use of flexure pivots 18 of a conventional type which may be obtained from the Fluid Power Division of Bendix, Utica, New York 13503. Flexure pivots 18 have a known spring constant, have a low restoring force so that they return to fixed center position, and yet rotate about a single axis, in this case the vertical axes 14, 16. The axes may be more generally defines as perpendicular to the plane in which the arms 10 and 12 pivot.

As is known these flexure pivots comprise coaxially located spring members cross-connected by diametrically disposed struts such that one interspring member can rotate or flex about the axis of the other cylindrical spring member. In this case the flexure pivots 18 are fitted into corresponding upper and lower (in the drawing) bores 20 in U-shaped base supports 26, 27 with an interference or friction fit. Longitudinal slots 22 and bores 21 formed in the respective arms 10 and 12, clamp the central pivotal portion of the pivots 18 which pivot relative to the outer end portions of each pivot so that the arms may pivot relative to the supports 26, 27. Clamping may be facilitated by screws 29 which reduce the width of the slots 22 upon tightening. Each of these slots may be terminated at either end if desired with additional bores 24 also formed in the arms 10 to facilitate this clamping action. The base supports 26, 27 are adjustably mounted on a base member or block 25. The base support 26 for the driving arm 12 has a slotted end piece in which is fitted a cam 28 and has its bore 21 fitted over a dowel pin (not shown) mounted in the block 25 so that the driving arm 12 may be adjusted pivotally about the pivot axis 16. Rotation of the cam 28 provides movement of the slotted end longitudinally of the arm 12 when a mounting screw 13 threaded into the base 25 is loosened, thereby adjusting the pivotal position of the arm 12. This facilitates centering of the driving arm relative to the position sensor, as will be described. The driven arm 10 is adjustable longitudinally by an adjusting screw 11 secured to a positioning block 15 which is slideably attached to the base 25 by a screw 17 fitted in a slot 19 in the block 15. A mounting screw 13 may be threaded into the base 25 to lock the base support 27 in position after adjustment. By these lateral and longitudinal adjustments, the arms may be adjusted to accommodate a sample 30 to be dynamically tested.

The sample 30 to be tested, say an elastomeric material, is adapted to be clamped by suitable sample clamps 32 between the respective arms 10 and 12. The sample clamps 32 as depicted in FIG. 1 are designed specifically for solid samples and may comprise generally U-shaped members 34 which are affixed to the test end of each of the arms 10 and 12 as by screws 36 and are adapted to contain clamping blocks 38 which are positionable as by screws 40 to grip or squeeze the ends of the sample 30. Alternate type clamps for fluid and charging viscosity materials will be described in conjunction with FIGS. 3 and 4.

The driven arm 10 is dynamically balanced about the pivot axis 14 as by the use of a counter weight 40 such that the moment of inertia on either side of the pivot axis 14 is identical. The driving arm 12 is structured such that it is dynamically balanced about the pivot axis 16 and the moments of inertia on either end of the arm relative to the axis 16 are identical. Such balancing in this instance primarily is done by properly shaping the arm. The driven end 44 of the driving arm 12 is actuated through a mechanical linkage indicated by the dashed line 46 by a suitable driver 48. Any known means for this purpose may be used. Typically an electromagnetic drive or electromechanical transducer of known type is used. One such transducer of this type is that described in said Shilling patent. As is described by Shilling, the driver 46–48 includes a magnetic armature on the arm 12 which is acted upon by an electromagnetic field generated through a driver coil wound about a slug (not shown). Preferably, a non-contact type electromechanical transducer which provides a constant driving force is used. A transducer of this type is described in copending application Ser. No. 662,270 filed Feb. 27, 1976 by John D. McGhee and uses a flat coil whose windings are position wholly without a uniform magnetic field.

A position sensor 50 may be mechanically linked, as depicted by the dashed line 52, to sense the displacement or position of the driving arm 12. It provides an output signal related to the natural or resonant frequency of the system to a feedback amplifier 54 which in turn actuates the driver 48 to provide an in-phase drive for the driving arm 12; i.e., in-phase with the lateral oscillations of the arm. Preferably, the feedback amplifier 54 should supply only the mechanical energy required to maintain the amplitude of ascillations constant. That is the energy supplied to the system is a measure of the damping losses caused by the sample under test.

A system for maintaining a constant amplitude vibration may be any known system such as that described for example in Gergen, U.S. Pat. No. 3,501,952 issued Mar. 24, 1970. Another system, which is preferred, is that described in the McGhee application. In this system the output of the displacement transducer is peak detected and applied to an integrator having as one input a reference voltage. The integrator thus provides a control output level, according to the relative amplitudes of the detected peaks and the reference voltage, which is used to control the driver to maintain the amplitude of the oscillations constant. Hence the output level of the integrator is a measure of sample damping. Alternatively, the feedback amplifier may operated with constant gain such that the amplitude of the output signal from the transducer 50 is a measure of system damping. The two arms 10 and 12 should be substantially equal in natural frequency.

In operation a sample of a material such as plastic to be tested is placed within by the sample clamps 32 and the screws 40 tightened to grip either end of the sample firmly such that the sample provides the only interconnection between the ends of the sample arms 10 and 12. The feedback amplifier 54 energizes the driver 48 to establish a lateral pivotal vibration within the driving arm 12. This movement is sensed by the position sensor 50 and provides an alternating current signal to the feedback amplifier which maintains the system in pivotal oscillation at a frequency determined by the inherent resonant frequency of the system. The amplifier merely supplies enough additional energy into the system to maintain the oscillations. These oscillations are controlled to have a constant amplitude as described. This permits the system damping to be measured as represented by the amplitude of the feedback signal from the amplifier 54. Alternatively, the amplitude of the transducer signal is a measure of damping as noted.

The resonant frequency of the system is determined in part by the moment of the two sample arms 10 and 12 together with the spring constant of the pivots 18 and the viscoelastic modulus E of the sample 30. The pivotal movement of the arms 10 and 12 causes the sample to undergo an arcuate motion while the ends of the sample are flexed in opposite directions as is described in the Shilling patent.

This apparatus is seen to have many advantages. Since the unit has a central pivot point for each of the sample arms and since the pivot has a relatively low torque, relatively low resonant frequencies in the order of 1 to 3 Hertz are obtainable. Because of this low frequency, the contribution of the sample as a percent of frequency change is greatly enhanced. An additional advantage is that the sample can be mounted at one end of the sample arms whereas the position sensors and drive mechanism may be located at the other at a point remote from any thermal chambers or ovens, depicted by the dashed rectangle 60, used to house the sample. Hence, they are not affected by the extreme temperatures of the thermal chamber. Because the arms are dynamically balanced, the susceptibility of the unit to vibration and shock is greatly reduced. Since the pivots are low torque the contribution of the sample to the system frequency is greater.

In a typical use application, a sample of linear high density polyethylene was clamped in the sample holders 34. The position of the arms 10, 12 is adjusted, as described previously, by cam 28 and screw 11 such that distance from the pivots to the sample are equal the position sensor is zeroed. The screws 17 and 13 permit different size samples to be accommodated by adjusting the lateral spacing between the arms. With the positioning adjustments completed, the arms and sample are set into vibration at the resonant frequency of the system. The temperature of the thermal chamber is varied and the output of the position sensor 50 (frequency) is recorded as is the amplitude output of the feedback amplifier 54 (damping) as a function of the temperature of the sample. A typical such use is depicted in the plot of FIG. 2 in which it may be noted that the frequency, which is related to the spring constant or real part of the modulus, decreases with increasing temperature. Likewise it may be noted that damping peaks at two different tempertures and may be related to the chemical bonding structure of the sample.

For testing materials which change their properties significantly over a period of time such as thermoset materials which undergo a drastic increase in modulus a sample holder such as shown in FIG. 3 may be used. A typical epoxy system will change its modulus from less than 10 dynes per $cm^2$ to more than $10^9$ dynes per $cm^2$ when setting. The sample holders for this system may comprise a pair of blocks 68 secured as by screws 36 to the sample ends of the arms 10, 12. Each block has a V-groove 70 machined therein. The V-grooves face up and each other so that an appropriate coiled spring 72 made of a suitable metal such as copper may be rested therein.

To effect the test of a liquid system, the spring 72 is first dipped in the liquid system and soaked with the material. The spring 72 is then placed in the V-grooves. The liquid sample adheres to the coiled spring by surface tension, with any excess liquid partially filling the groove thereby insuring adequate holding as the sample solidifies. The system is energized and the test run as previously described. Following the test, the coiled spring is pulled from the grooves and the grooves cleaned. In a typical case No. 34 copper wire wound on a 0.1524 centimeter diameter cylindrical form at 20 turns per centimeter functioned well. This sample holder has the advantages of being of reproducible geometry, having sufficient flexibility to cover the full range of modulus under test, and being easily cleaned after a test.

For samples which are more fluid, the parallel plates 74 depicted in FIG. 4 may be substituted for the clamps depicted in FIG. 1. These plates 74, which may be made of any suitable material such as stainless steel, are secured to the sample ends of the sample arms 10 and 12 by the screws 36 such that that plates lie one below the other (when the arms are horizontal) both within the general plane of vibration of the sample arms 10 and 12. Each plate has a central raised portion 76 which provides the actual sample contact, the remainder of the plates serving to contain any fluid spill-over. The raised portion is generally rectangular and thus defines the surface area over which the fluid sample is applied. Thus if a sample is placed between the plates, the sample undergoes shear stress as the plates move back and forth relative to each other generally along axes that are both longitudinal of and transverse to the axes of the sample arms as the sample arms move from side to side. Positioning of the arms and implementation of the test is accomplished as previously described —to in this case, the coupling between the arms being the fluid.

The apparatus described has broad application to the polymer characterization field among others. Having a wide modulus range, it can follow curing throughout the entire range from fluid to solid. It can measure second order low energy transitions which appear as both a damping peak (FIG. 2) and a modulus change. Such transitions are of particular importance in the elastomer areas, e.g., the tire industry since mechanical damping is a measure of the energy dissipation or heat generated by the elastomer in say a tire. Different type polymer and elastomer materials are often blended or grafted to each other to enhance thier properties such as impact resistance, etc. The measure of this effect can be correlated with the damping peaks. A temperature plot (FIG. 2) of a polymer provides information regarding the morphological properties of the polymer. The damping transitions referred to as second order relaxation processes, are a result of specific molecular reorientations and are a key to information on the structural and physical properties of the polymer.

In alternative embodiments, a bearing or other free type pivot may be used in place of the flexure pivots. Such pivots are useful with solid samples, but difficulty is encountered with fluid samples since there is too little restoring force to maintain oscillations. It should also be noted that the apparatus may be driven at constant or programmed frequency if desired. As still another alternative the pivots may be placed at one end of the arms instead of the center.

We claim:

1. Apparatus for analyzing the dynamic properties of a sample comprising, in combination,
   a pair of spaced, elongated members for engaging said sample therebetween,
   pivot means for pivotally mounting said members for lateral in-phase pivotal motion generally in a common plane,
   drive means for subjecting one of said members and hence, through said sample, the other of said members to vibratory motion in said plane, and
   sensing means responsive to the movement of one of said members for providing a signal corresponding to said vibratory motion.

2. Apparatus as set forth in claim 1 wherein said pivot means are flexure pivots each having a known spring constant.

3. Apparatus as set forth in claim 2 wherein said elongated members each are dynamically balanced about their respective said pivot means.

4. Apparatus as set forth in claim 5 wherein said sample and said drive means are positioned axially of said members on opposite sides of said pivot means.

5. Apparatus as set forth in claim 4 wherein said sample and said sensing means are positioned axially of said members on opposite sides of said pivot means.

6. Apparatus as set forth in claim 5 wherein said members each have clamp means at one end for gripping said sample as spaced portions.

7. Apparatus as set forth in claim 2 wherein said sample and said drive means are positioned axially of said members on opposite sides of said pivot means.

8. Apparatus as set forth in claim 2 wherein said sample and said sensing means are positioned axially of said members on opposite sides of said pivot means.

9. Apparatus as set forth in claim 1 wherein said elongated members each are dynamically balanced about their respective said pivot means and each have substantially the same natural frequency.

10. Apparatus as set forth in claim 1 wherein said sample and said drive means are positioned axially of said members on opposite sides of said pivot means.

11. Apparatus as set forth in claim 1 wherein said sample and said sensing means are positioned axially of said members on opposite sides of said pivot means.

12. Apparatus as set forth in claim 1 wherein said members each have a planar sample plate at one end oriented to lie parallel to said common plane, said plates having contiguous faces adapted to receive a fluid sample therebetween.

13. Apparatus as set forth in claim 1 wherein said pivot means are fixed.

14. Apparatus as set forth in claim 13 which includes means for laterally positioning one of said pivot means to adjust said members for different sized samples.

15. Apparatus as set forth in claim 13 which includes means for positioning one of said pivot means longitudinally of said members.

* * * * *